US012714448B2

(12) United States Patent
Chung et al.

(10) Patent No.: US 12,714,448 B2
(45) Date of Patent: Aug. 25, 2026

(54) EXTRACORPOREAL SHOCK WAVE DEVICE FOR LOADING TARGET SUBSTANCE INTO DELIVERY VEHICLE

(71) Applicant: EXOLLENCE CO., LTD., Seoul (KR)

(72) Inventors: Jihwa Chung, Gimpo-si (KR); Minyoung Lee, Seoul (KR)

(73) Assignee: EXOLLENCE CO., LTD., Seoul (KR)

( * ) Notice: Subject to any disclaimer, the term of this patent is extended or adjusted under 35 U.S.C. 154(b) by 333 days.

(21) Appl. No.: 18/288,030

(22) PCT Filed: Oct. 13, 2023

(86) PCT No.: PCT/KR2023/015828
§ 371 (c)(1),
(2) Date: Oct. 23, 2023

(87) PCT Pub. No.: WO2025/005349
PCT Pub. Date: Jan. 2, 2025

(65) Prior Publication Data

US 2025/0082349 A1 Mar. 13, 2025

(30) Foreign Application Priority Data

Jun. 28, 2023 (KR) ........................ 10-2023-0083595

(51) Int. Cl.
*A61B 18/26* (2006.01)
*A61B 17/22* (2006.01)
(Continued)

(52) U.S. Cl.
CPC .. *A61B 17/22022* (2013.01); *A61B 17/22029* (2013.01); *A61B 17/2255* (2013.01); *A61B 18/245* (2013.01); *A61B 18/26* (2013.01); *A61B 2017/00867* (2013.01); *A61B 2017/22014* (2013.01); *A61B 2017/22024* (2013.01);
(Continued)

(58) Field of Classification Search
CPC ....... C12M 1/06; C12M 1/42; A61B 17/2255; A61B 17/22029; A61B 18/26; A61B 18/245; A61B 17/22022; A61B 2017/22014; A61B 2017/2212; A61B 2017/22039; A61B 2017/00867; A61B 2017/22079; A61B 2017/22084; A61B 2017/22025; A61B 2017/22054; A61B 2017/22024
See application file for complete search history.

(56) References Cited

U.S. PATENT DOCUMENTS 5,301,659 A * 4/1994 Brisson .............. A61B 17/2255 601/4
2011/0034832 A1* 2/2011 Cioanta .................. A61B 18/26 601/1
(Continued)

FOREIGN PATENT DOCUMENTS

KR 10-2020-0136978 A 12/2020

*Primary Examiner* — Abdallah Abulaban
*Assistant Examiner* — Amie M Ndure
(74) *Attorney, Agent, or Firm* — Han's Law Office

(57) ABSTRACT

The present invention relates to an extracorporeal shock wave device for loading a target substance into a delivery vehicle. According to the present invention, the time taken to load the target substance into the delivery vehicle can be significantly reduced, and the loading rate can also be greatly improved.

12 Claims, 16 Drawing Sheets

(51) Int. Cl.

| | |
|---|---|
| ***A61B 17/225*** | (2006.01) |
| ***A61B 18/24*** | (2006.01) |
| *A61B 17/00* | (2006.01) |
| *A61B 17/221* | (2006.01) |

(52) U.S. Cl.
CPC ............... *A61B 2017/22025* (2013.01); *A61B 2017/22039* (2013.01); *A61B 2017/22054* (2013.01); *A61B 2017/22079* (2013.01); *A61B 2017/22084* (2013.01); *A61B 2017/2212* (2013.01)

(56) References Cited

U.S. PATENT DOCUMENTS

2017/0202595 A1* 7/2017 Shelton, IV ........... A61B 18/00
2017/0202605 A1* 7/2017 Shelton, IV ............ H01M 6/02
2019/0201047 A1* 7/2019 Yates ..................... H04N 7/183

* cited by examiner

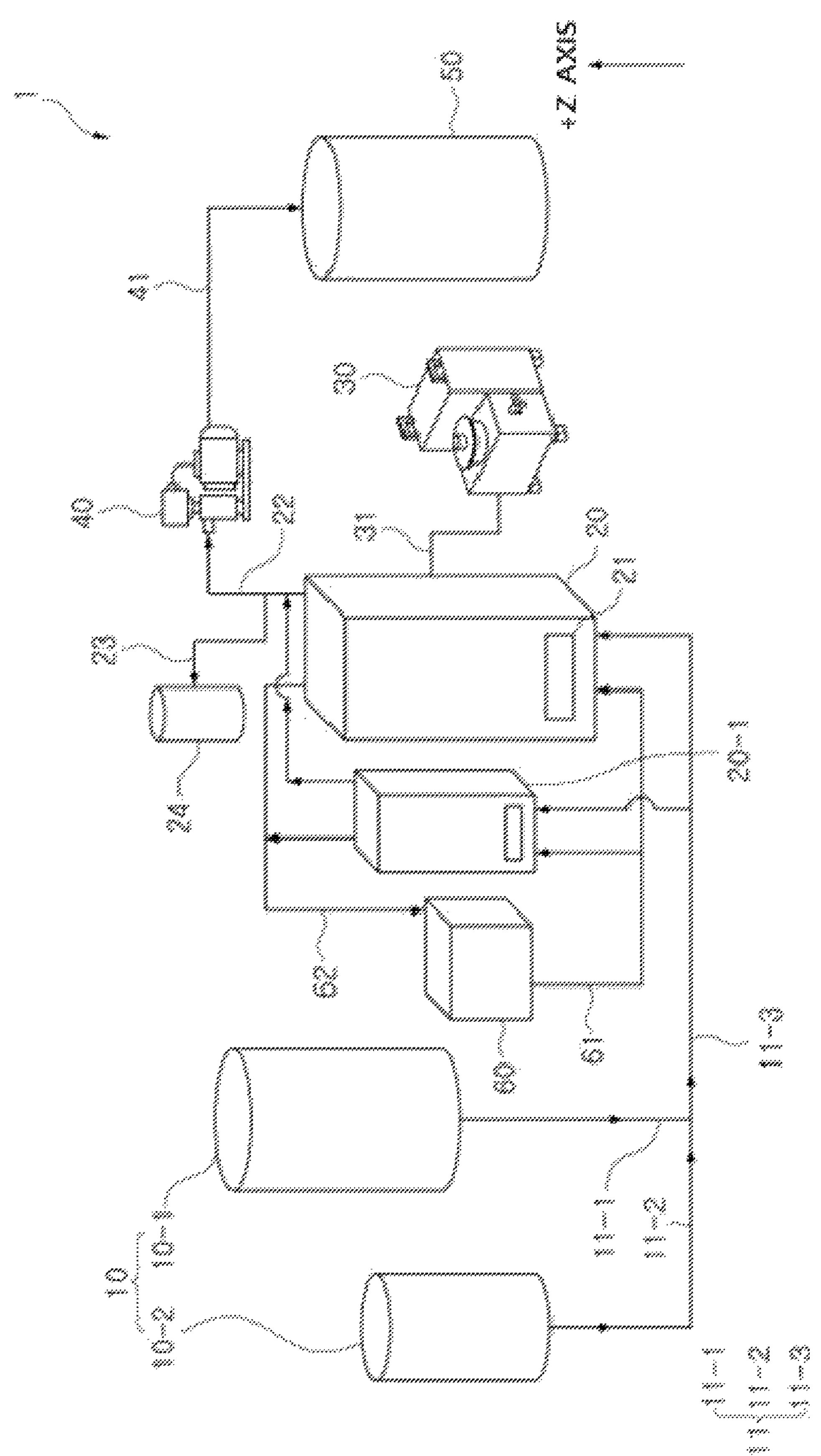
[FIG. 1]

[FIG. 2]
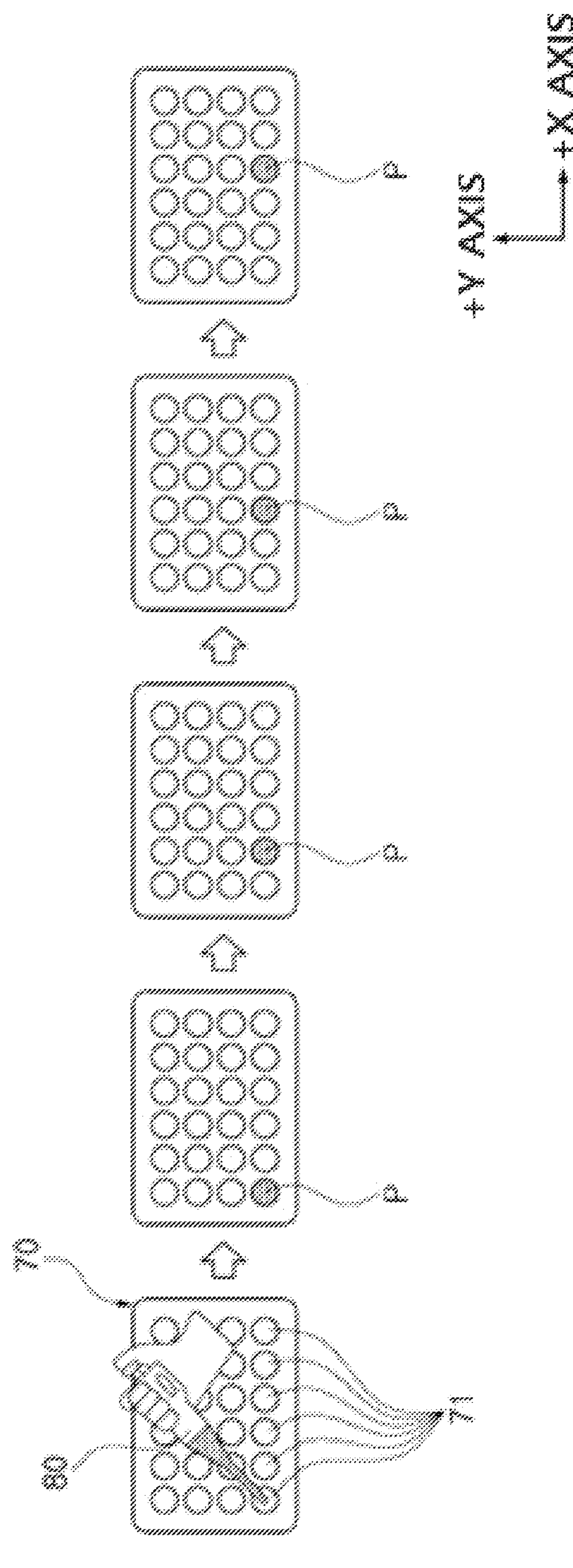

[FIG. 3]
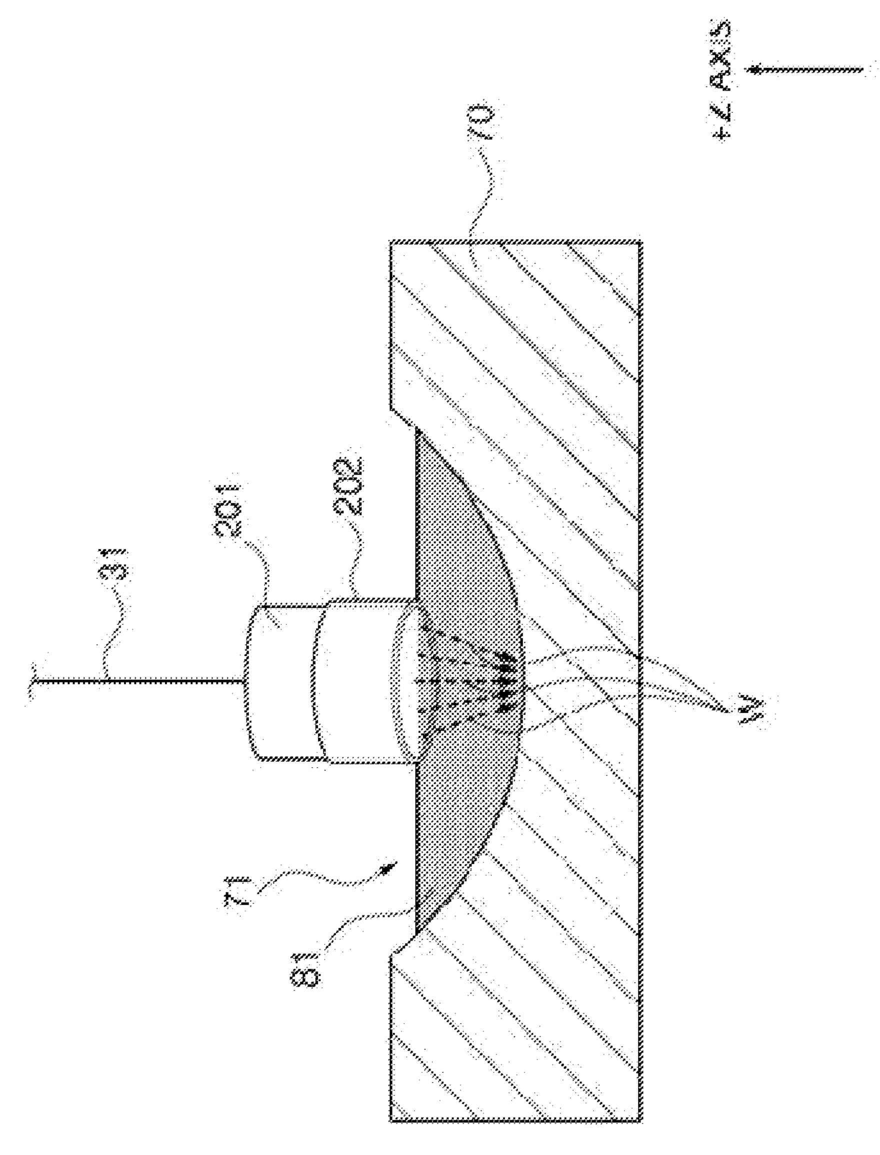

[FIG. 4]
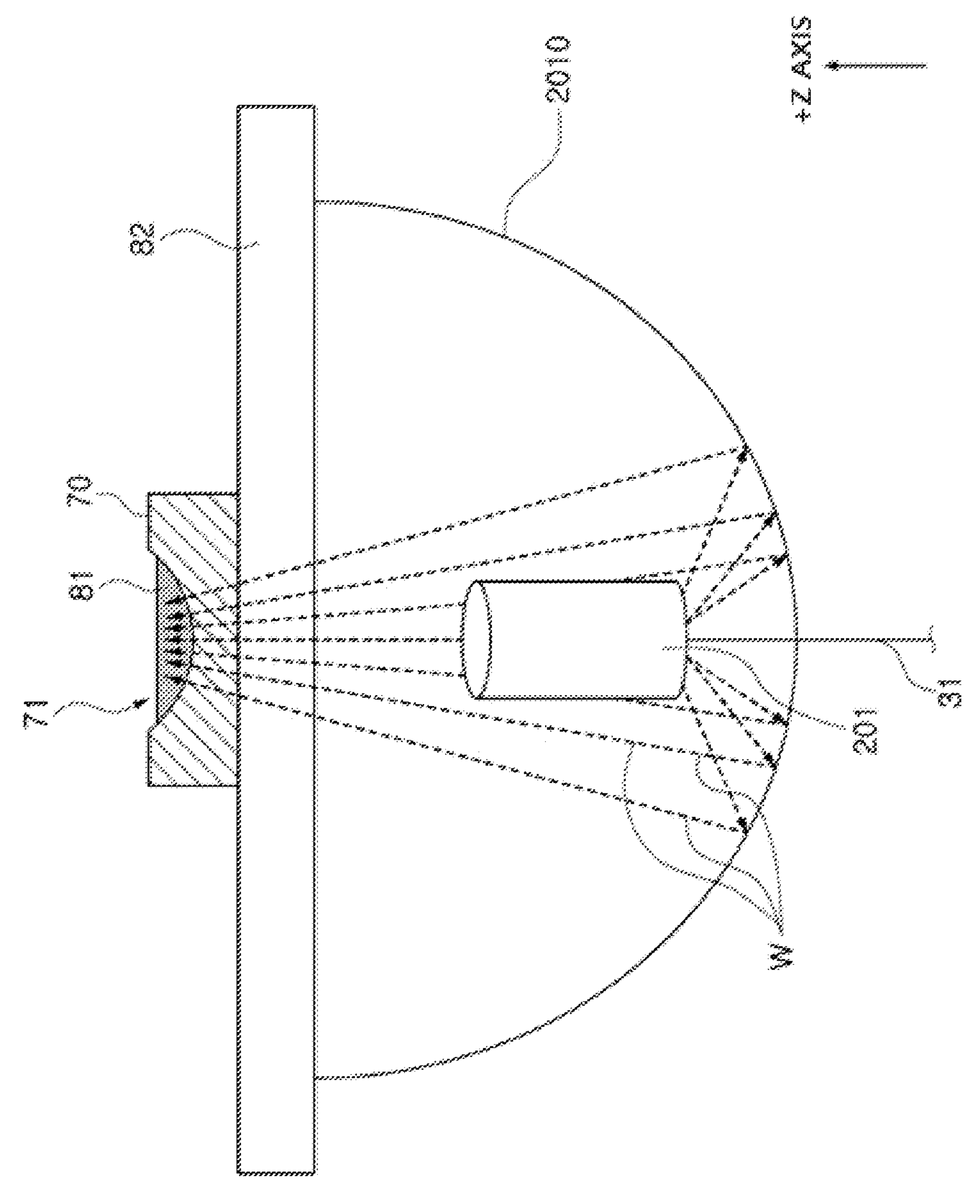

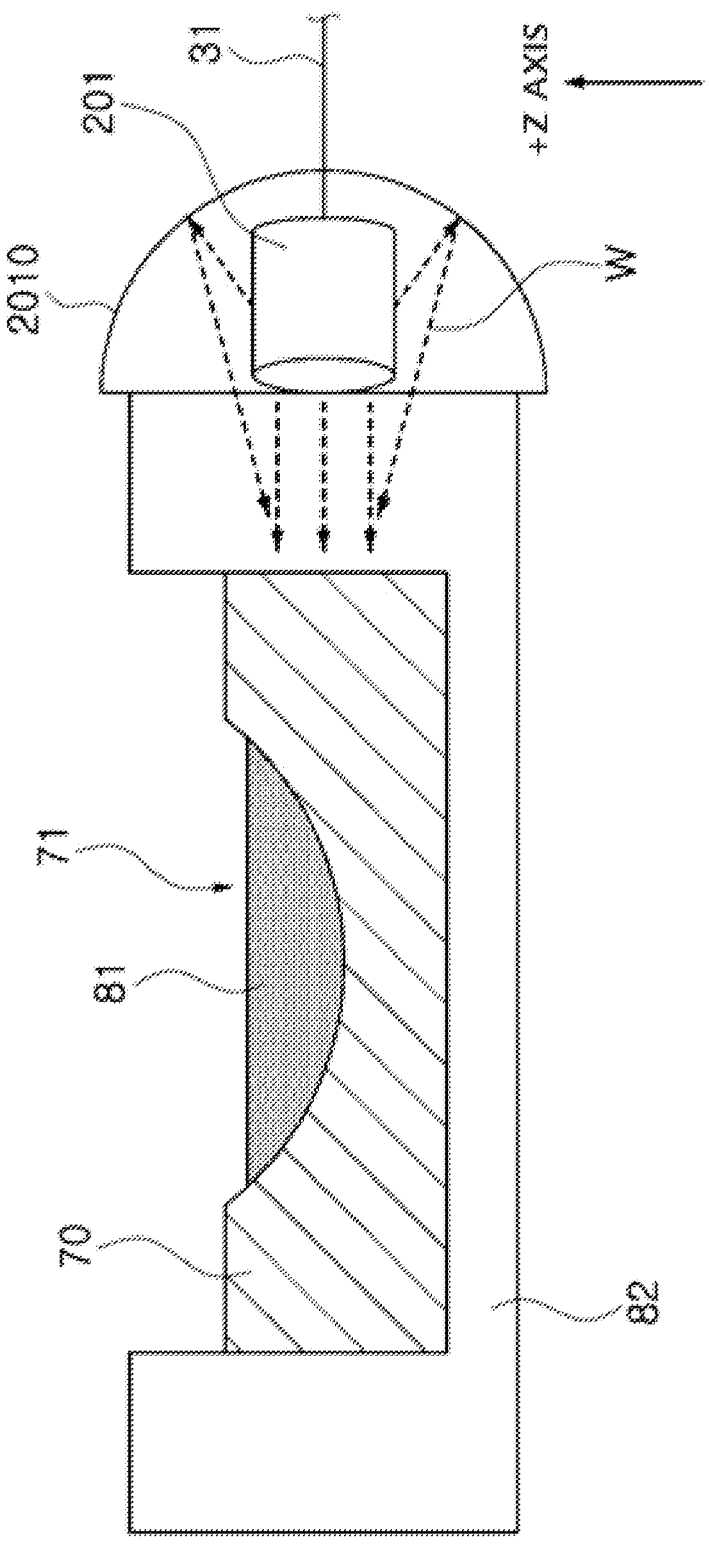
[FIG. 5]

[FIG. 6]
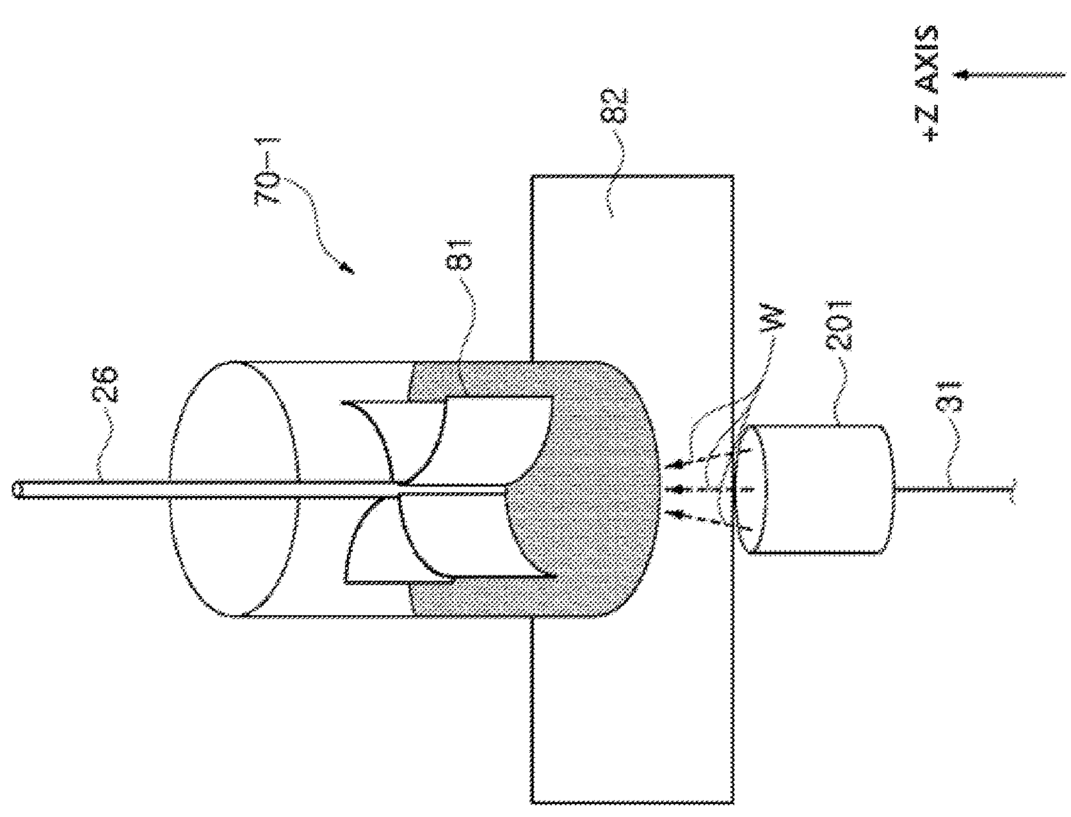

[FIG. 7]
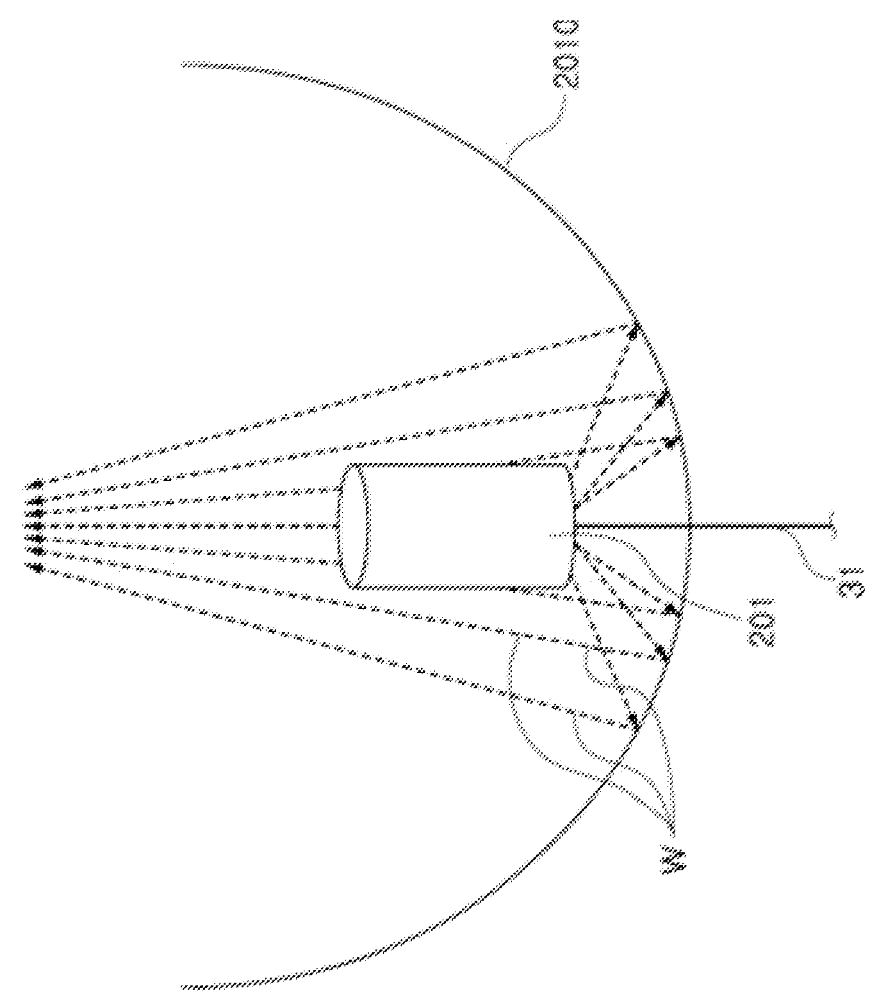

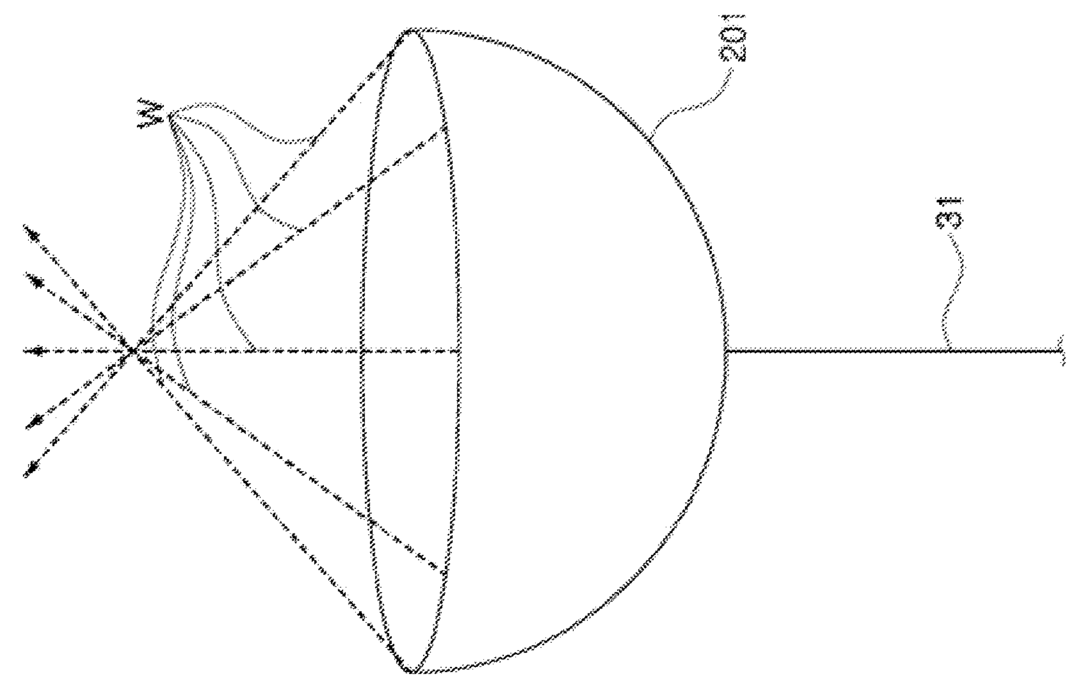
[FIG. 8]

[FIG. 11]
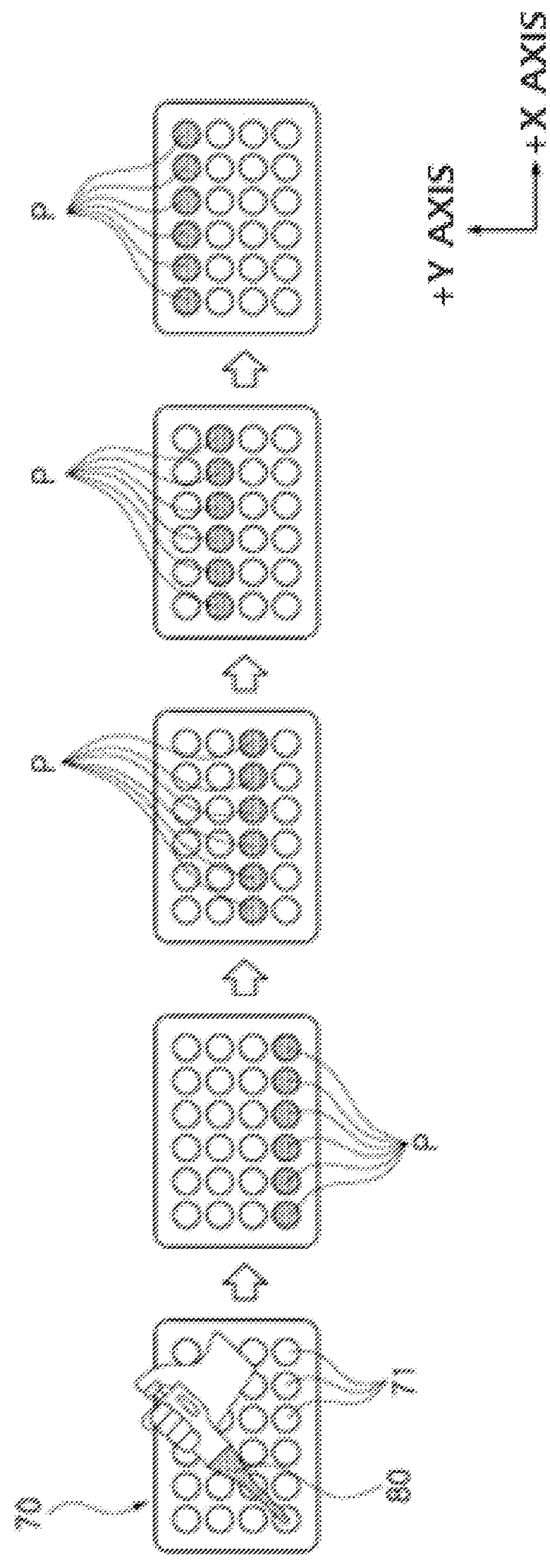

[FIG. 12]
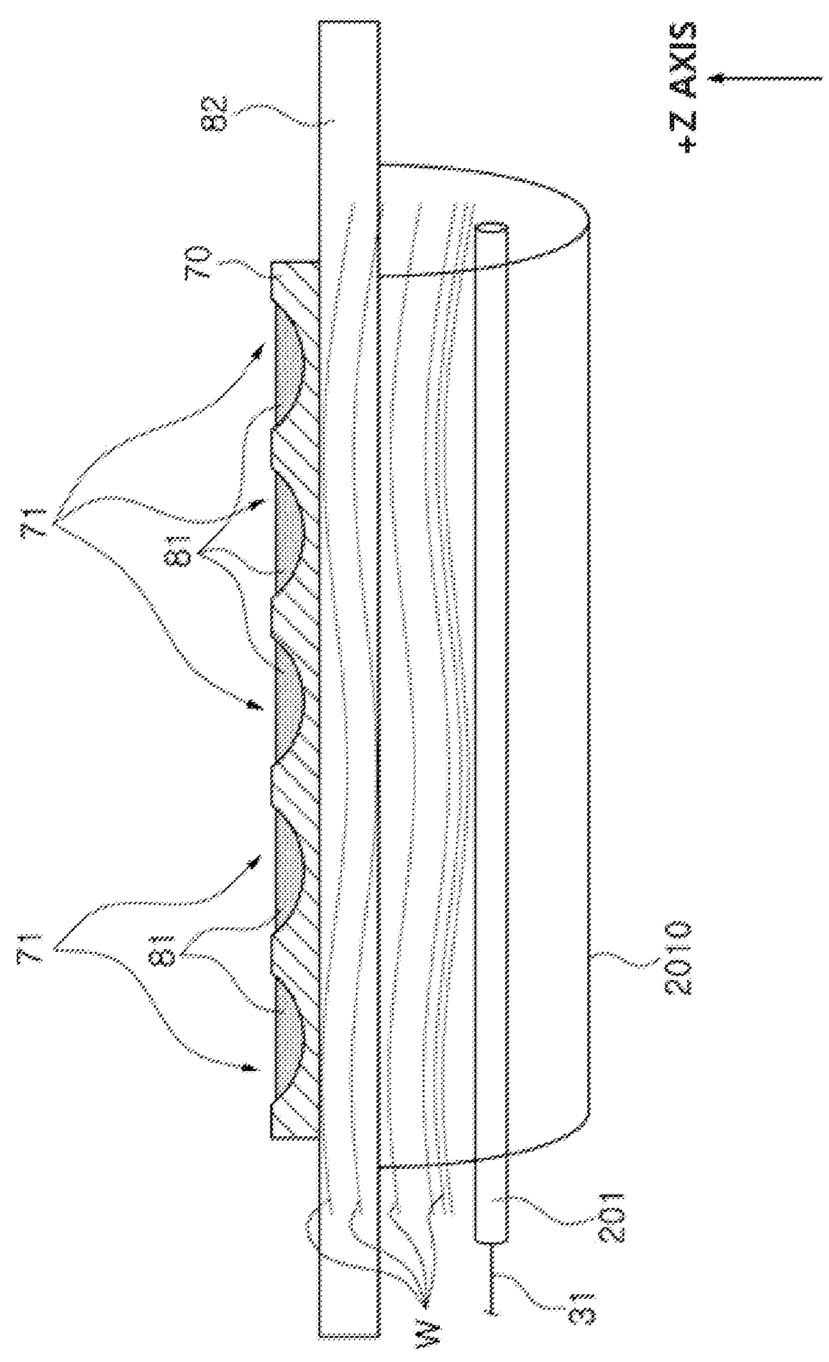

[FIG. 13]

+Z AXIS
82
70
71
81
201
W
71
81
201
W

[FIG. 15]
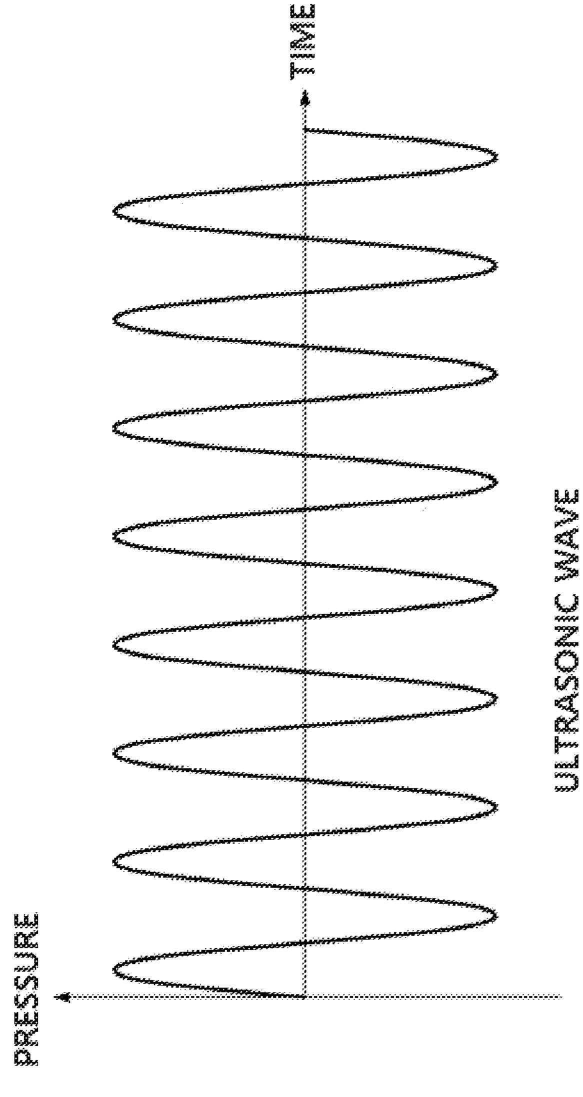

[FIG. 16]
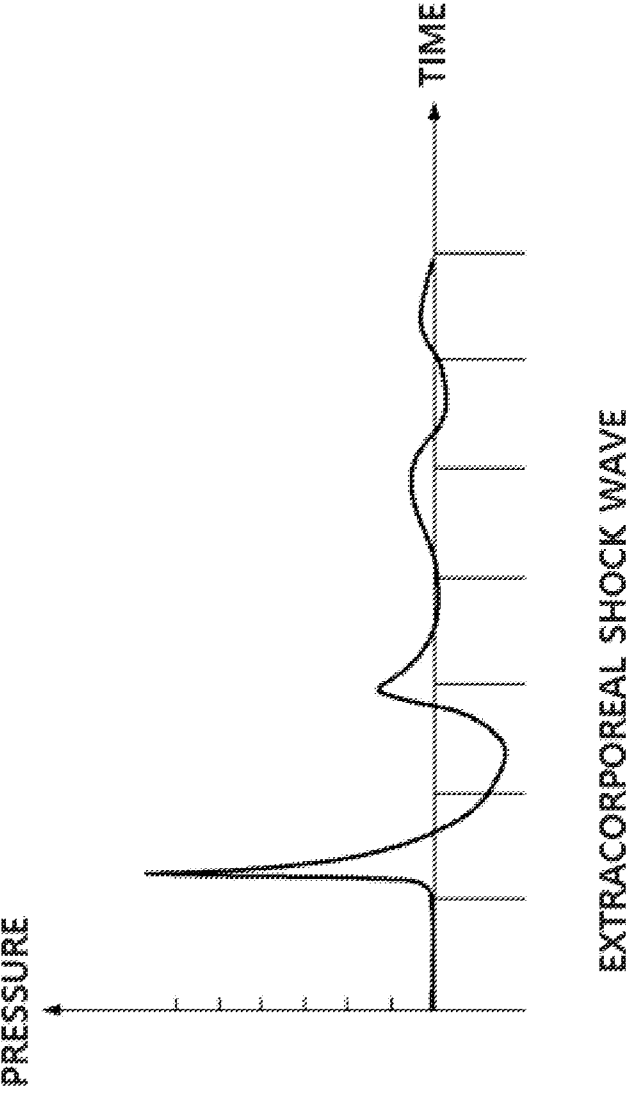

EXTRACORPOREAL SHOCK WAVE DEVICE FOR LOADING TARGET SUBSTANCE INTO DELIVERY VEHICLE

TECHNICAL FIELD

The present invention relates to an extracorporeal shock wave device that loads a target substance into a delivery vehicle.

BACKGROUND ART

When a disease occurs in the human body, it is important to ensure that a drug reaches a desired area within the human body at the correct time. To achieve this, a method of loading a target substance (drug) into a liposome, such as a lipid bilayer, which has a structure similar to a membrane of an organelle within a cell and delivering the liposome loaded with the target substance to a predetermined site is used.

Since the liposome used in this method is not a substance that originally is present in the human body, an immune response to the liposome may occur in the human body. An extracellular vesicle is being discussed as an alternative to the liposome to deliver the target substance to the predetermined site while avoiding such immune response.

The extracellular vesicle is a type of vesicle released to the outside of the cell and serves to deliver biological substances such as proteins, fats, metabolites, and nucleic acids to recipient cells. It is considered that the role of the extracellular vesicle is likely to replace the liposome.

Electroporation may be used to load the target substance into the extracellular vesicle, but electroporation has problems in that the loading rate of the target substance into the extracellular vesicle is low and the loading time is long.

The background technology of the invention is disclosed in Korean Patent Application Publication No. 10-2020-0136978 (published on Dec. 8, 2020, Title of the Invention: Use of exosome for targeted delivery of therapeutic agent).

DISCLOSURE

Technical Problem

The present invention is directed to providing an extracorporeal shock wave device capable of not only reducing the time to load a target substance into a delivery vehicle but also greatly improving the loading rate.

Technical Solution

One aspect of the present invention provides an extracorporeal shock wave device for loading a target substance into a delivery vehicle, the device including an extracorporeal shock wave generator, a transmission member connected to the extracorporeal shock wave generator, and an extracorporeal shock wave transduction unit including an extracorporeal shock wave transducer that converts power supplied from the extracorporeal shock wave generator through the transmission member into extracorporeal shock waves, wherein the extracorporeal shock wave transducer radiates extracorporeal shock waves and loads a target substance inside a solution into a delivery vehicle.

The extracorporeal shock wave device may further include an inlet formed in at least a portion of the extracorporeal shock wave generator, and a transduction container in which at least one transduction container hole is formed, wherein the solution may be accommodated in the transduction container hole, and the transduction container may be inserted into the inlet.

The extracorporeal shock wave transducer and the transduction container may move relative to each other.

The extracorporeal shock wave device may further include a protective member that surrounds at least a portion of the extracorporeal shock wave transducer, wherein the protective member and the solution may be in contact with each other.

The extracorporeal shock wave device may further include a refrigerant supply flow path that is connected to the extracorporeal shock wave transduction unit and supplies a refrigerant to the extracorporeal shock wave transduction unit, a refrigerant discharge flow path that is connected to the extracorporeal shock wave transduction unit and moves the refrigerant discharged from the extracorporeal shock wave transduction unit, and a cooler that is connected to the refrigerant supply flow path and the refrigerant discharge flow path and cools the refrigerant.

The extracorporeal shock wave transducer may be disposed under the transduction container, the refrigerant may be disposed between the extracorporeal shock wave transducer and the transduction container, and extracorporeal shock waves generated by the extracorporeal shock wave transducer may proceed to the transduction container hole.

The extracorporeal shock wave device may further include a reflective plate that surrounds at least a portion of the extracorporeal shock wave transducer, wherein the extracorporeal shock waves generated by the extracorporeal shock wave transducer may be reflected by the reflective plate and proceed to the transduction container hole.

The extracorporeal shock wave transducer may have a longitudinal direction, and a reflective plate may have a longitudinal direction parallel to the longitudinal direction of the extracorporeal shock wave transducer.

The extracorporeal shock wave device may further include at least one supply container in which the delivery vehicle or the target substance is accommodated, a first flow path which is connected to the supply container and the extracorporeal shock wave transduction unit and through which the delivery vehicle or the target substance accommodated in the supply container moves to the extracorporeal shock wave transduction unit, a refrigerant supply flow path which is connected to the extracorporeal shock wave transduction unit and through which a refrigerant is supplied to the extracorporeal shock wave transduction unit, a refrigerant discharge flow path which is connected to the extracorporeal shock wave transduction unit and through which the refrigerant discharged from the extracorporeal shock wave transduction unit moves, a cooler that is connected to the refrigerant supply flow path and the refrigerant discharge flow path and cools the refrigerant, a second flow path through which the solution discharged from the extracorporeal shock wave transduction unit moves, a pump that is connected to the second flow path and moves the solution, a third flow path which is connected to the second flow path and through which a portion of the solution moves to a sample storage container, and a fourth flow path which is connected to the pump and a storage container and through which the solution moves to the storage container.

The extracorporeal shock wave transduction unit may further include a transduction flow path through which the solution moves and which has a longitudinal direction, at least a portion of the transduction flow path may be in contact with the refrigerant, and the extracorporeal shock wave transducer may be in contact with the refrigerant.

A longitudinal direction of a transduction flow path may be parallel to a vertical direction, and the solution may move from one side to the other side of the transduction flow path.

A longitudinal direction of a transduction flow path may be perpendicular to a vertical direction, and the solution may move from one side to the other side of the transduction flow path.

The extracorporeal shock wave device may further include a stirrer disposed inside the transduction flow path.

The extracorporeal shock wave device may further include a second extracorporeal shock wave transducer that converts the power supplied through the transmission member into extracorporeal shock waves and is connected to the extracorporeal shock wave transducer in parallel.

Advantageous Effects

According to the present invention, the time taken to load a target substance into a delivery vehicle can be significantly reduced, and the loading rate can also be greatly improved.

DESCRIPTION OF DRAWINGS

FIG. 1 is a perspective view of an extracorporeal shock wave device according to one embodiment of the present invention.

FIG. 2 is a plan view illustrating transduction containers according to one embodiment of the present invention.

FIG. 3 illustrates a transducer disposed on an upper side of the transduction container according to the present invention.

FIG. 4 illustrates a transducer disposed on a lower side of the transduction container according to the present invention.

FIG. 5 illustrates a transducer disposed on a side surface of the transduction container according to the present invention.

FIG. 6 illustrates a transducer disposed on the lower side of the container according to the present invention.

FIGS. 7 and 8 illustrate embodiments of an extracorporeal shock wave transducer.

FIG. 9 illustrates an extracorporeal shock wave generated by the extracorporeal shock wave transducer according to the present invention and transmitted to a plurality of tubes.

FIG. 10 illustrates the extracorporeal shock wave generated by the extracorporeal shock wave transducer according to the present invention and transmitted to the plurality of tubes.

FIG. 11 is a plan view of the transduction containers according to the embodiment of the present invention.

FIG. 12 illustrates a transducer disposed on a lower side of the transduction container according to the present invention.

FIG. 13 illustrates the extracorporeal shock wave transducer disposed on the lower side of the transduction container according to the present invention.

FIG. 14 illustrates an embodiment in which a reflective plate is disposed in the extracorporeal shock wave transducer according to the present invention.

FIG. 15 illustrates a pressure change due to ultrasonic waves over time.

FIG. 16 illustrates a pressure change due to extracorporeal shock waves over time.

MODES OF THE INVENTION

Hereinafter, an extracorporeal shock wave device for loading a target substance into a delivery vehicle according to the present invention will be described with reference to the accompanying drawings. In this process, the thickness of lines or the size of components illustrated in the drawings may be exaggerated for clarity and convenience of description. Further, terms described below are defined in consideration of functions in the present invention and may change according to the intentions or customs of a user or an operator. Therefore, definitions of these terms should be made based on the contents throughout the present specification.

FIG. 1 is a perspective view of an extracorporeal shock wave device according to one embodiment of the present invention.

An extracorporeal shock wave device 1 (hereinafter, referred to as an "extracorporeal shock wave device") may include a supply container 10, a first flow path 11, an extracorporeal shock wave transduction unit 20, an extracorporeal shock wave generator 30, a pump 40, a storage container 50, a cooler 60, and a transduction container (e.g., a transduction container 70 of FIG. 3).

According to the embodiment, the supply container 10 may include a first supply container 10-1 and a second supply container 10-2. The first supply container 10-1 and/or the second supply container 10-2 may accommodate target substances including proteins, ribonucleic acid (RNA), and the like and/or delivery vehicles including extracellular vesicles, liposomes, and the like.

According to the embodiment, the first flow path 11 may include a 1-1 flow path 11-1, a 1-2 flow path 11-2, and a 1-3 flow path 11-3. The first supply container 10-1 may be connected to the 1-1 flow path 11-1, and the second supply container 10-2 may be connected to the 1-2 flow path 11-2. Contents accommodated in the first supply container 10-1 may be discharged through the 1-1 flow path 11-1. Contents accommodated in the second supply container 10-2 may be discharged through the 1-2 flow path 11-2. The 1-1 flow path 11-1 may be connected to the 1-3 flow path 11-3, and the 1-2 flow path 11-2 may be connected to the 1-3 flow path 11-3. The 1-3 flow path 11-3 may be connected to the extracorporeal shock wave transduction unit 20. In this way, as the first supply container 10-1 and/or the second supply container 10-2 are connected to the extracorporeal shock wave transduction unit 20 through the first flow path 11, the contents in the first supply container 10-1 and/or the contents in the second supply container 10-2 may move from the first supply container 10-1 and/or the second supply container 10-2 to the extracorporeal shock wave transduction unit 20.

Although FIG. 1 illustrates the first supply container 10-1 and the second supply container 10-2, the supply container 10 may include two or more supply containers. Each supply container 10 may be connected to the 1-3 flow path 11-3 connected to the extracorporeal shock wave transduction unit 20 through a flow path. Accordingly, the contents accommodated inside each supply container 10 may be delivered to the extracorporeal shock wave transduction unit 20.

According to an embodiment, the target substance and the delivery vehicle may be accommodated in one supply container 10, and according to another embodiment, the target substance and the delivery vehicle may be accommodated in separate supply containers 10.

According to the embodiment, the extracorporeal shock wave transduction unit 20 may transmit shock waves to the target substance and delivery vehicle delivered from the supply container 10. The extracorporeal shock wave transduction unit 20 may be connected to the extracorporeal shock wave generator 30 through a transmission member 31. The extracorporeal shock wave generator 30 may be connected to a power source to supply energy to the extracorporeal shock wave transduction unit 20 through the transmission member 31, and the extracorporeal shock wave transduction unit 20 may convert the energy transferred from the extracorporeal shock wave generator 30 to generate extracorporeal shock waves. The extracorporeal shock waves generated through the extracorporeal shock wave transduction unit 20 may be transmitted to the delivery vehicle and the target substance, so that the target substance may be loaded into the delivery vehicle.

According to another embodiment, an inlet 21 may be formed in at least a portion of the extracorporeal shock wave transduction unit 20. The transduction container (e.g., the transduction container 70 in FIG. 2) may be inserted into the extracorporeal shock wave transduction unit 20 through the inlet 21. The transduction container 70 may accommodate the delivery vehicle and the target substance. The transduction container 70 in which the delivery vehicle and the target substance are accommodated may be inserted into the extracorporeal shock wave transduction unit 20, the extracorporeal shock waves generated by the extracorporeal shock wave transduction unit 20 may be transmitted to the delivery vehicle and the target substance accommodated in the transduction container 70, and thus the target substance may be loaded into the delivery vehicle.

The extracorporeal shock wave transduction unit 20 may be connected to a refrigerant supply flow path 61 and a refrigerant discharge flow path 62, and the refrigerant supply flow path 61 and the refrigerant discharge flow path 62 may be connected to the cooler 60. A refrigerant may flow into the extracorporeal shock wave transduction unit 20 through the refrigerant supply flow path 61 and cool the heat generated by the extracorporeal shock wave transduction unit 20, and the refrigerant may flow out of the extracorporeal shock wave transduction unit 20 through the refrigerant discharge flow path 62. The refrigerant discharged from the extracorporeal shock wave transduction unit 20 through the refrigerant discharge flow path 62 may flow into the cooler 60, be cooled, and then flow into the extracorporeal shock wave transduction unit 20 through the refrigerant supply flow path 61. The refrigerant may be used as a medium for transmitting the extracorporeal shock waves generated by the extracorporeal shock wave transduction unit 20. According to the embodiment, the refrigerant may be water.

According to the embodiment, a second extracorporeal shock wave transduction unit 20-1 may be connected in parallel to the extracorporeal shock wave transduction unit 20. The second extracorporeal shock wave transduction unit 20-1 may be connected in parallel to the extracorporeal shock wave transduction unit 20 and thus increase a capacity per hour of loading the target substance into the delivery vehicle in the extracorporeal shock wave device 1. The second extracorporeal shock wave transduction unit 20-1 may be connected to the first flow path 11 and may receive the target substance and/or the delivery vehicle including an extracellular vesicle, a liposome, or the like from the supply container 10. In addition to the second extracorporeal shock wave transduction unit 20-1, a plurality of extracorporeal shock wave transduction units may be provided. The second extracorporeal shock wave transduction 20-1 may be the same as or similar to the extracorporeal shock wave transduction unit 20.

A description of the extracorporeal shock wave transduction unit 20 will be made below together with descriptions of FIGS. 3, 4, 5, 6, 12, and 14.

The extracorporeal shock wave transduction unit 20 may be connected to a second flow path 22. The second flow path 22 may connect the extracorporeal shock wave transduction unit 20 and the pump 40. The second flow path 22 may be connected to a third flow path 23. The third flow path 23 may be connected to a sample storage container 24. With this configuration, the delivery vehicle into which the target substance is loaded in the extracorporeal shock wave transduction unit 20 may be delivered to the sample storage container 24 and/or the pump 40 through the second flow path 22 and/or the third flow path 23. By inspecting a solution contained in the sample storage container 24, the quality of the solution contained in the storage container 50 can be identified.

The pump 40 may receive power and move the solution containing the delivery vehicle loaded with the target substance delivered from the second flow path 22 to the storage container 50. The pump 40 may be a peristaltic pump and may accurately control the amount of fluid transferred per hour. It is illustrated that the pump 40 is connected to the second flow path 22, but the pump 40 may be disposed in the first flow path 11, the third flow path 23, the refrigerant supply flow path 61 and/or the refrigerant discharge flow path 62. The pump 40 may be connected to a fourth flow path 41.

The fourth flow path 41 may connect the pump 40 and the storage container 50. The pump 40 may deliver the solution containing the delivery vehicle loaded with the target substance to the storage container 50 through the fourth flow path 41.

Figure 9:
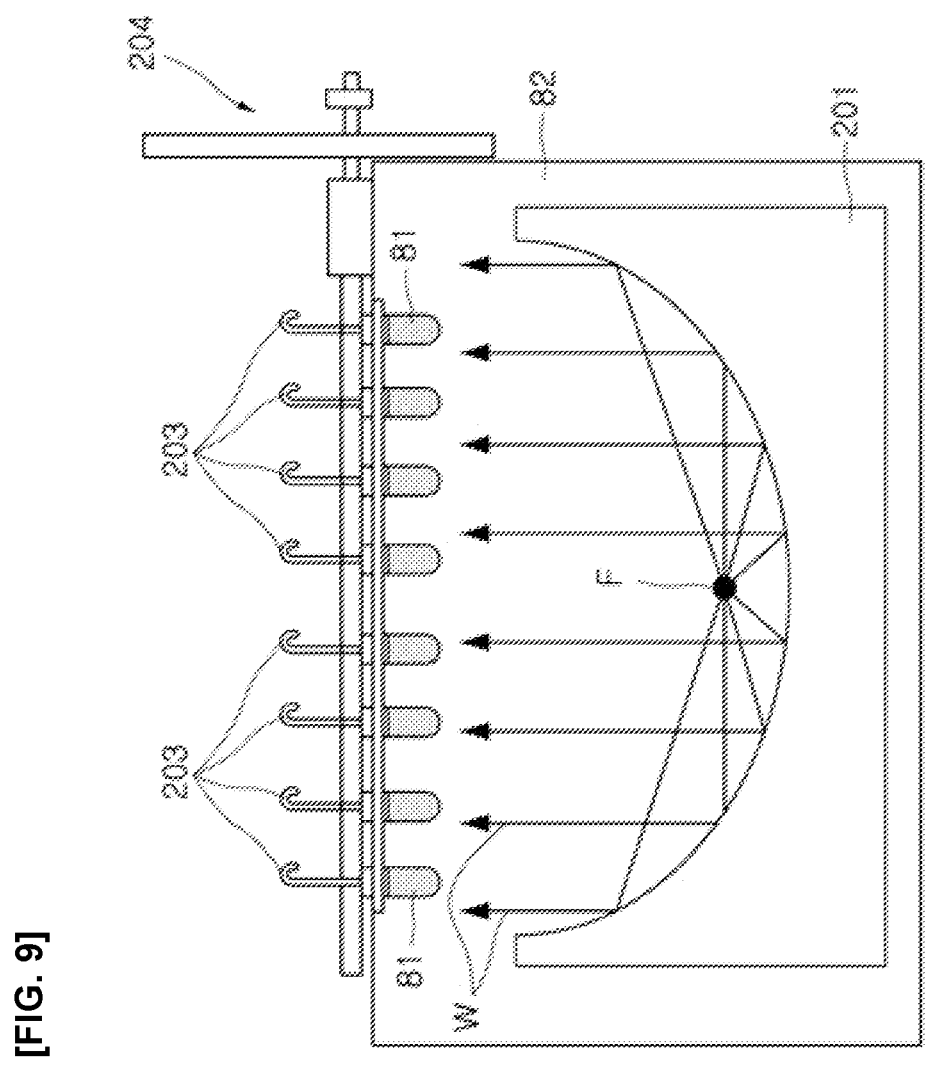
Figure 10:
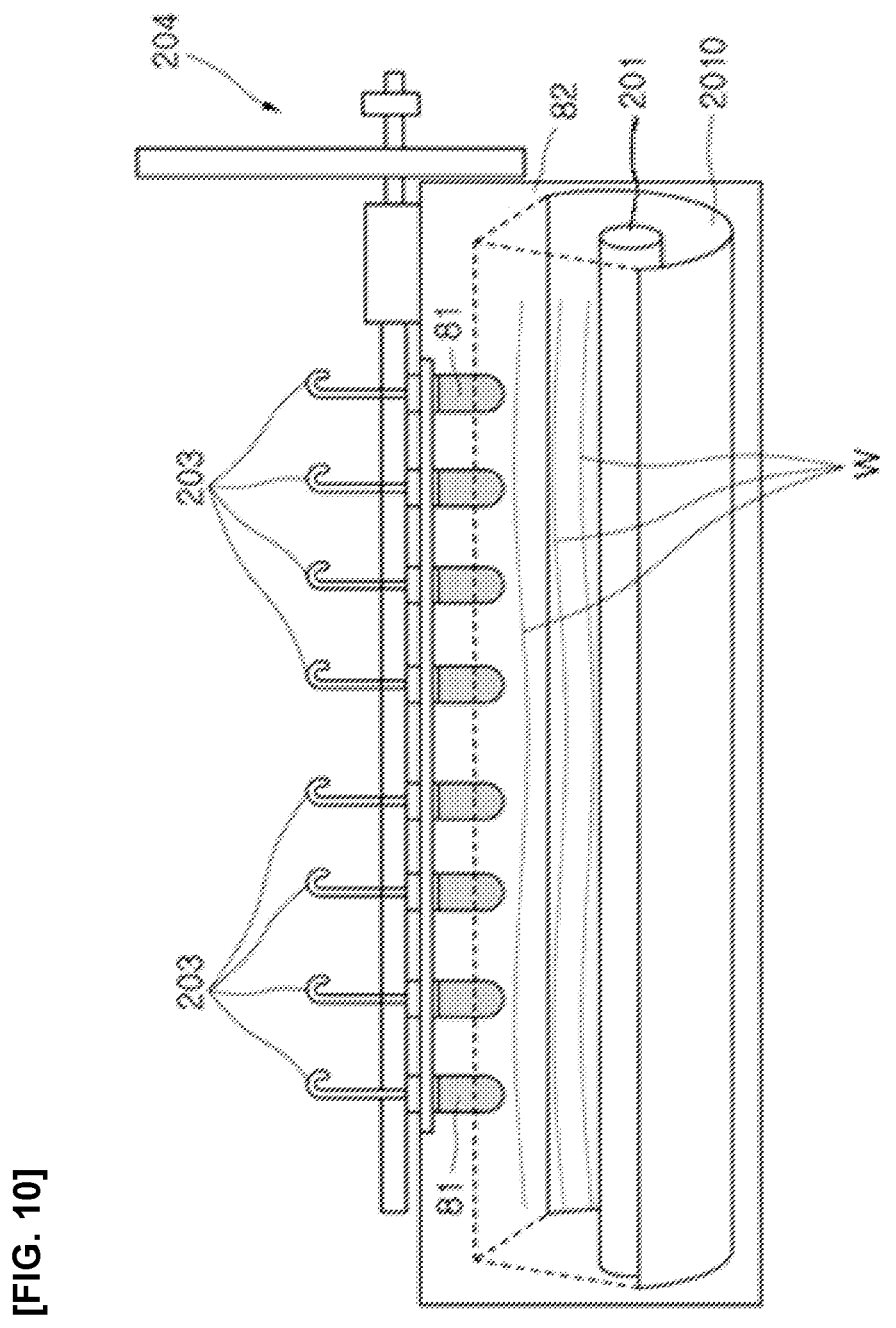

FIG. 2 is a plan view illustrating transduction containers according to one embodiment of the present invention, FIG. 3 illustrates a transducer disposed on an upper side of the transduction container according to the present invention, FIG. 4 illustrates a transducer disposed on a lower side of the transduction container according to the present invention, FIG. 5 illustrates a transducer disposed on a side surface of the transduction container according to the present invention, FIG. 6 illustrates a transducer disposed on the lower side of the container according to the present invention, FIGS. 7 and 8 illustrate an embodiment of an extracorporeal shock wave transducer, FIG. 9 illustrates an extracorporeal shock wave generated by the extracorporeal shock wave transducer according to the present invention and transmitted to a plurality of tubes, and FIG. 10 illustrates the extracorporeal shock wave generated by the extracorporeal shock wave transducer according to the present invention and transmitted to the plurality of tubes.

Referring to FIG. 2, according to various embodiments, the transduction container 70 inserted into the inlet 21 formed in the extracorporeal shock wave transduction unit 20 can be identified.

The transduction container 70 may include at least one transduction container hole 71. According to the embodiment, the transduction container 70 may include a plurality of transduction container holes 71 formed in rows and columns. The transduction container hole 71 may accommodate a solution discharged from an injector 80. The injector 80 can accommodate and discharge the solution containing the delivery vehicle and the target substance. The solution discharged from the injector 80 may be accommodated in the transduction container hole 71, and the transduction container 70 may be inserted into the extracorporeal shock wave transduction unit 20 through the inlet 21.

Inside the extracorporeal shock wave transduction unit 20, an extracorporeal shock wave transducer (e.g., an extracorporeal shock wave transducer 201 of FIG. 3) connected to the transmission member 31 generates extracorporeal shock waves, and the transduction container 70 may be irradiated with the extracorporeal shock waves. An extracorporeal shock wave irradiation position P, where the extracorporeal shock waves are radiated by the extracorporeal shock wave transducer 201, may be changed.

The solution is accommodated in at least one transduction container hole 71, the transduction container 70 is inserted into the extracorporeal shock wave transduction unit 20, and then the solution accommodated in the transduction container hole 71 may be irradiated with extracorporeal shock waves. The extracorporeal shock wave irradiation position P may change according to movement of the extracorporeal shock wave transducer 201 or movement of the transduction container 70.

According to one embodiment, the extracorporeal shock wave transducer 201 may radiate only one transduction container hole 71 with extracorporeal shock waves. Referring to FIG. 2, an embodiment in which, at the extracorporeal shock wave irradiation position P, only one transduction container hole 71 is irradiated can be identified. It can be identified that the extracorporeal shock wave irradiation position P moves to the right from the transduction container hole 71 at the bottom left. A pattern in which the extracorporeal shock wave irradiation position P is changed may be changed according to the purpose and necessity of an experiment.

Referring to FIG. 3, the extracorporeal shock wave transducer 201 connected to the transmission member 31 can be identified. The extracorporeal shock wave transducer 201 may be surrounded by a protective member 202. The protective member 202 may prevent direct contact between the extracorporeal shock wave transducer 201 and a solution 81 accommodated in the transduction container hole 71, thereby preventing contamination of the solution 81.

The extracorporeal shock wave transducer 201 may be disposed above the transduction container 70 (e.g., in a +Z axis direction) and immersed in the solution 81 accommodated in the transduction container hole 71. The extracorporeal shock wave transducer 201 immersed in the solution 81 may generate extracorporeal shock waves W. The extracorporeal shock waves W generated by the extracorporeal shock wave transducer 201 may be transmitted toward the solution 81. The extracorporeal shock waves W generated by the extracorporeal shock wave transducer 201 may be radiated to be concentrated toward a portion of the solution 81. The target substance inside the solution 81 may be loaded into the delivery vehicle by the extracorporeal shock waves W. The extracorporeal shock wave transducer 201 illustrated in FIG. 3 may be implemented as an extracorporeal shock wave transducer 201 provided with a reflective plate 2010 illustrated in FIG. 7 or an extracorporeal shock wave transducer 201 having a shape similar to a curved surface illustrated in FIG. 8, and thus the extracorporeal shock waves W generated by the extracorporeal shock wave transducer 201 may be concentrated at a predetermined focus.

Referring to FIG. 4, the extracorporeal shock wave transducer 201 connected to the transmission member 31 may be disposed at a lower portion (e.g., in a-Z axis direction) of the transduction container 70. The extracorporeal shock wave transducer 201 may be surrounded by the reflective plate 2010. The reflective plate 2010 may be formed in a curved shape. As the extracorporeal shock wave transducer 201 is surrounded by the reflective plate 2010, the extracorporeal shock waves W generated by the extracorporeal shock wave transducer 201 may be reflected by the reflective plate 2010 and concentrated at a predetermined position.

The extracorporeal shock waves W generated by the extracorporeal shock wave transducer 201 may proceed to a medium 82. Alternatively, the extracorporeal shock waves W may be reflected by the reflective plate 2010 and proceed to the medium 82. The medium 82 may be in contact with the extracorporeal shock wave transducer 201 and accommodated in a space formed inside the reflective plate 2010. The extracorporeal shock waves W may pass through the medium 82 and the transduction container 70 and may be concentrated at at least a portion of the solution 81 disposed in the transduction container hole 71. In this way, even when the extracorporeal shock wave transducer 201 is disposed under the transduction container 70, the extracorporeal shock waves W may be transmitted to the solution 81 through the medium 82. Accordingly, the target substance inside the solution 81 may be loaded into the delivery vehicle. The refrigerant may function as the medium 82.

Referring to FIG. 5, the extracorporeal shock wave transducer 201 connected to the transmission member 31 may be disposed on a side surface of the transduction container 70. The extracorporeal shock waves W generated by the extracorporeal shock wave transducer 201 may pass through the medium 82 and/or the transduction container 70 and may be radiated to the solution 81. The extracorporeal shock waves W may be concentrated at a portion of the solution 81. The extracorporeal shock waves W radiated to the portion of the solution 81 may load the target substance inside the solution 81 into the delivery vehicle.

Referring to FIG. 6, the transduction container 70 may be implemented in the form of a single transduction container 70-1. The single transduction container 70-1 may accommodate the solution 81. At least a portion of the single transduction container 70-1 may be in contact with the medium 82, and the extracorporeal shock wave transducer 201 connected to the transmission member 31 may transmit the extracorporeal shock waves W to the single transduction container 70-1 through the medium 82. The extracorporeal shock waves W may load the target substance inside the solution 81 into the delivery vehicle.

The extracorporeal shock waves W generated by the extracorporeal shock wave transducer 201 may proceed to the medium 82. The medium 82 may be in contact with the extracorporeal shock wave transducer 201 and the transduction container 70. The transduction container 70 may include the single transduction container 70-1. The extracorporeal shock waves W may pass through the medium 82 and the transduction container 70 and may be concentrated at at least a portion disposed inside the solution 81. In this way, even when the extracorporeal shock wave transducer 201 is disposed outside the transduction container 70, the extracorporeal shock waves W may be transmitted to the solution 81 through the medium 82. Accordingly, the target substance inside the solution 81 may be loaded into the delivery vehicle.

As the extracorporeal shock wave transducer 201 is disposed on the side surface of the transduction container 70, the extracorporeal shock waves W may be transmitted to the delivery vehicle and the target substance disposed on a side surface of the transduction container hole 71. According to one embodiment, cells are disposed in the solution 81 accommodated inside the transduction container hole 71, and even when the cells are adhered to the side surface of the transduction container hole 71, the extracorporeal shock waves W are effectively transmitted, and thus the target substance may be loaded into the cells or inserted into the cells.

A stirrer 26 may be disposed inside the single transduction container 70-1. The stirrer 26 may stir the solution 81 contained in the single transduction container 70-1 to make the solution 81 uniform.

FIGS. 7 and 8 illustrate embodiments of the extracorporeal shock wave transducer.

Referring to FIG. 7, the reflective plate 2010 may be disposed outside the extracorporeal shock wave transducer 201. The extracorporeal shock waves W generated by the extracorporeal shock wave transducer 201 may be reflected by the reflective plate 2010 and concentrated in a predetermined space. In this way, as the extracorporeal shock waves W are concentrated in the predetermined space, an energy density per unit area in the space in which the extracorporeal shock waves W are concentrated may increase.

Referring to FIG. 8, the extracorporeal shock wave transducer 201 may be implemented in a roughly hemispherical shape. The extracorporeal shock waves W may be generated by the hemispherical extracorporeal shock wave transducer 201, and the generated extracorporeal shock waves W may be concentrated in a predetermined space. In this way, as the extracorporeal shock waves W are concentrated in the predetermined space, the energy density per unit area in the space in which the extracorporeal shock waves W are concentrated may increase.

FIG. 9 illustrates extracorporeal shock waves generated by the extracorporeal shock wave transducer of the present invention, which are transmitted to the plurality of tubes.

The extracorporeal shock wave transduction unit 20 may include a jig 204. The jig 204 may hold one or more tubes 203. The solution 81 may be accommodated inside the tube 203, and at least a portion of the tube 203 may be in contact with the medium 82.

The extracorporeal shock wave transducer 201 may generate the extracorporeal shock waves W, and the generated extracorporeal shock waves W may be transmitted to the tube 203 and the solution 81 accommodated in the tube 203 through the medium 82. According to the embodiment, the extracorporeal shock wave transducer 201 illustrated in FIG. 8 may be a piezo type or an electromagnetic type. The extracorporeal shock waves W may be transmitted to the target substance and the delivery vehicle accommodated in the solution 81, and the target substance may be loaded into the delivery vehicle.

FIG. 10 illustrates the extracorporeal shock waves generated by the extracorporeal shock wave transducer of the present invention, which are transmitted to the plurality of tubes. The extracorporeal shock wave transduction unit 20 may include the jig 204. The jig 204 may hold one or more tubes 203. The solution 81 may be accommodated inside the tube 203, and at least a portion of the tube 203 may be in contact with the medium 82.

The extracorporeal shock wave transducer 201 may generate the extracorporeal shock waves W, and the generated extracorporeal shock waves W may be transmitted to the tube 203 and the solution 81 accommodated in the tube 203 through the medium 82. According to one embodiment, the reflective plate 2010 may be disposed outside the extracorporeal shock wave transducer 201 illustrated in FIG. 7. The extracorporeal shock waves W generated by the extracorporeal shock wave transducer 201 may be reflected by the reflective plate 2010 and transmitted to the solution 81 accommodated in the tube 203. The extracorporeal shock waves W may be transmitted to the target substance and the delivery vehicle accommodated in the solution 81, and the target substance may be loaded into the delivery vehicle.

Figure 13:
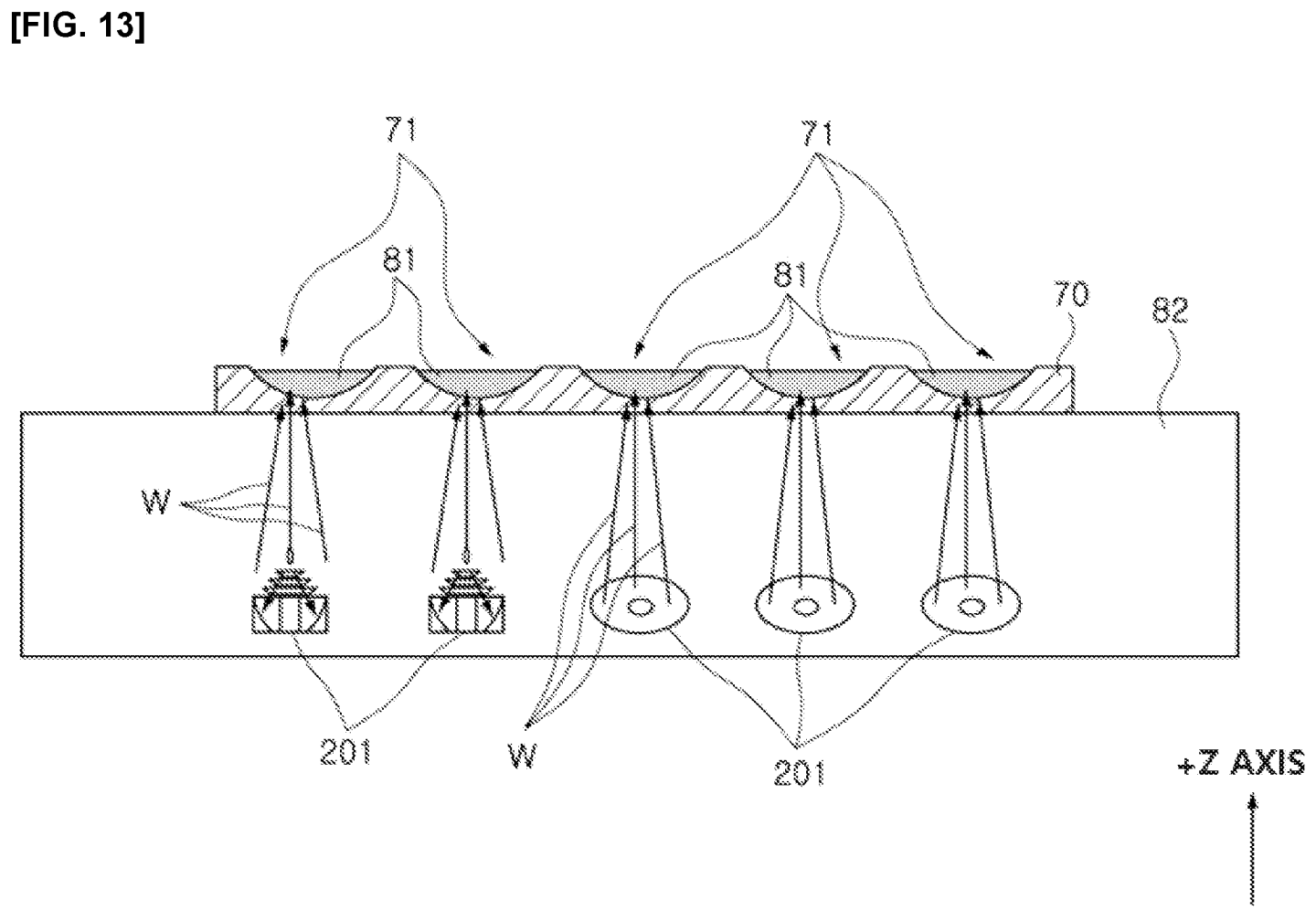

FIG. 11 is a plan view of the transduction containers according to the embodiment of the present invention, FIG. 12 illustrates a transducer disposed on a lower side of the transduction container according to the present invention, and FIG. 13 illustrates the transducer disposed on the lower side of the transduction container according to the present invention.

The extracorporeal shock wave transducer 201, the reflective plate 2010, the transmission member 31, the transduction container 70, the transduction container hole 71, the solution 81, and the medium 82 illustrated in FIGS. 11 and 12 may be the same as or similar to the extracorporeal shock wave transducer 201, the reflective plate 2010, the transmission member 31, the transduction container 70, the transduction container hole 71, the solution 81, and the medium 82 illustrated in FIGS. 1 to 5. Thus, descriptions of the same configurations will be omitted.

Referring to FIG. 11, according to various embodiments, the transduction container 70 inserted into the inlet 21 formed in the extracorporeal shock wave transduction unit 20 can be identified.

The transduction container 70 may include at least one transduction container hole 71. According to the embodiment, the transduction container 70 may include a plurality of transduction container holes 71 formed in rows and columns.

Inside the extracorporeal shock wave transduction unit 20, the extracorporeal shock wave transducer (e.g., an extracorporeal shock wave transducer 201 of FIG. 12) connected to the transmission member 31 generates the extracorporeal shock waves, and the transduction container 70 may be irradiated with the extracorporeal shock waves. The extracorporeal shock wave irradiation position P, where the extracorporeal shock waves are radiated by the extracorporeal shock wave transducer 201, may be changed. The extracorporeal shock wave irradiation position P may change according to the movement of the extracorporeal shock wave transducer 201 or the movement of the transduction container 70.

According to one embodiment, the extracorporeal shock wave transducer 201 may radiate a plurality of transduction container holes 71 with the extracorporeal shock waves W. Referring to FIG. 11, an embodiment in which, at the extracorporeal shock wave irradiation position P, the plurality of transduction container holes 71 are irradiated can be identified. It can be identified that the extracorporeal shock wave irradiation position P moves from the transduction container holes 71 disposed at the bottom of the transduction container 70 to the transduction container holes 71 disposed at the top of the transduction container 70. A pattern in which the extracorporeal shock wave irradiation position P is changed may be changed according to the purpose and necessity of the experiment. In this way, the solution 81 arranged in the plurality of transduction container holes 71 is irradiated with the extracorporeal shock waves W through one extracorporeal shock wave transducer 201, and thus the time required to radiate the extracorporeal shock waves W may be reduced.

Referring to FIG. 12, the extracorporeal shock wave transducer 201 connected to the transmission member 31 and configured to have a longitudinal direction may be disposed at a lower portion (e.g., in the −Z axis direction) of the transduction container 70. The extracorporeal shock waves W generated by the extracorporeal shock wave transducer 201 may be transmitted to the solution 81. The extracorporeal shock wave transducer 201 configured to have a longitudinal direction may be surrounded by the reflective plate 2010 configured to have a longitudinal direction. The reflective plate 2010 may be formed in a curved shape. As the extracorporeal shock wave transducer 201 is surrounded by the reflective plate 2010, the extracorporeal shock waves W generated by the extracorporeal shock wave transducer 201 may be reflected by the reflective plate 2010 and concentrated at a predetermined position inside the plurality of transduction container holes 71.

The extracorporeal shock waves W generated by the extracorporeal shock wave transducer 201 may proceed to the medium 82. Alternatively, the extracorporeal shock waves W may be reflected by the reflective plate 2010 and proceed to the medium 82. The medium 82 may be in contact with the extracorporeal shock wave transducer 201 and accommodated in the space formed inside the reflective plate 2010. The extracorporeal shock waves W may pass through the medium 82 and the transduction container 70 and may be concentrated at at least a portion inside the solution 81 disposed in each transduction container hole 71. In this way, even when the extracorporeal shock wave transducer 201 is disposed under the transduction container 70, the extracorporeal shock waves W may be transmitted to the solution 81 through the medium 82. Accordingly, the target substance inside the solution 81 may be loaded into the delivery vehicle. Further, the time required to radiate the extracorporeal shock waves W may be reduced.

Referring to FIG. 13, the extracorporeal shock wave transducer 201 that radiates the solution 81 accommodated in the transduction container hole 71 of the transduction container 70 with extracorporeal shock waves W may be provided. The extracorporeal shock wave transducer 201 may be a piezo type and/or an electromagnetic type. The extracorporeal shock waves W generated by the piezo type and/or electromagnetic type extracorporeal shock wave transducer 201 may pass through the medium 82 and be radiated toward a predetermined focus. The solution 81 may be disposed at a predetermined focus at which the extracorporeal shock waves W converge.

Figure 14:
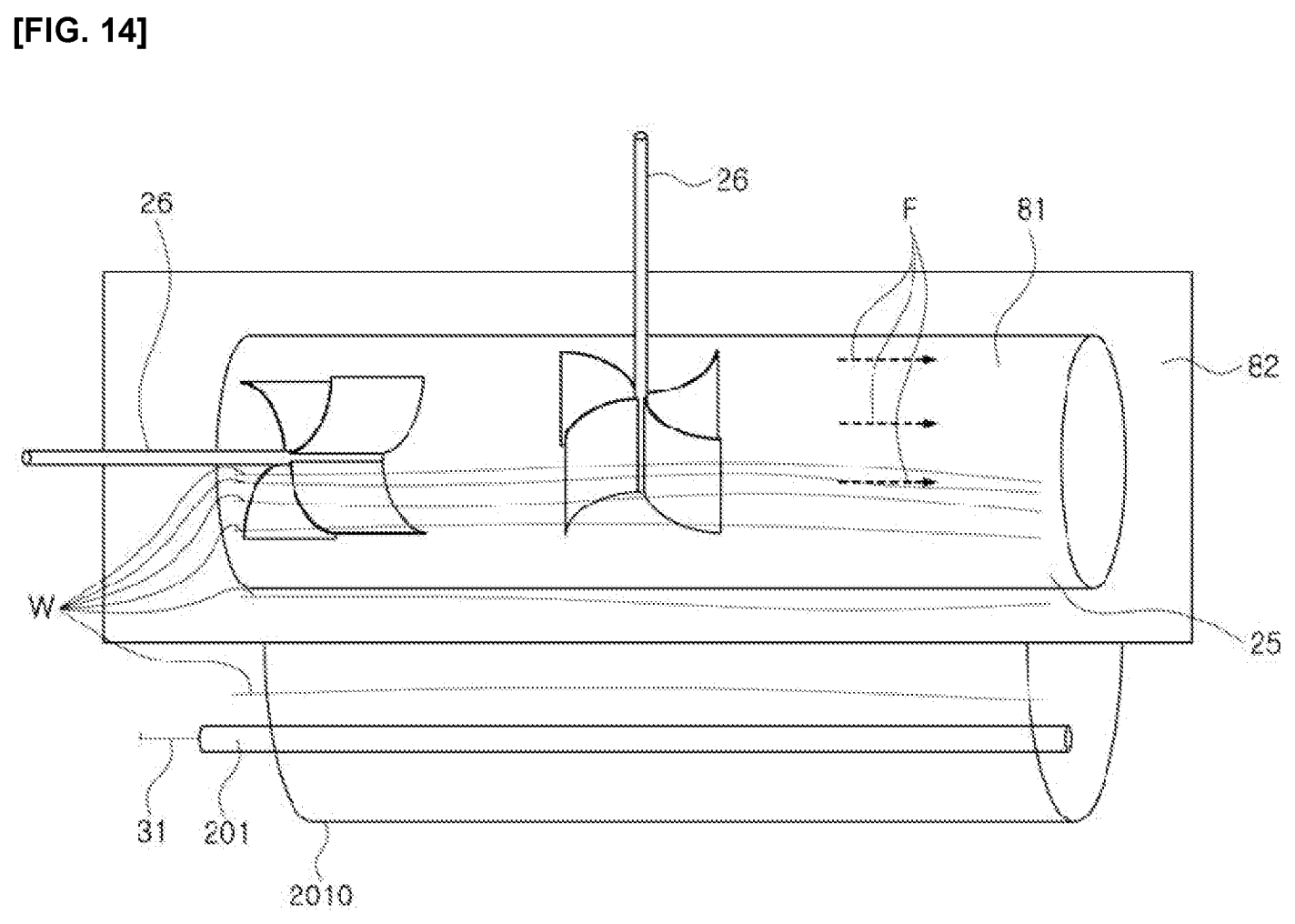

FIG. 14 illustrates an embodiment in which a reflective plate is disposed in the extracorporeal shock wave transducer according to the present invention.

The extracorporeal shock wave transducer 201, the reflective plate 2010, the transmission member 31, the solution 81, and the medium 82 illustrated in FIG. 14 may be the same as or similar to the extracorporeal shock wave transducer 201, the reflective plate 2010, the transmission member 31, the solution 81, and the medium 82 illustrated in FIGS. 1 to 12. Thus, descriptions of the same configurations will be omitted.

Referring to FIG. 14, it can be identified that the solution 81 flows in a solution flow direction F through a transduction flow path 25. The flow direction F in FIG. 14 may be implemented in a direction horizontal or perpendicular to the ground. According to one embodiment, the solution flow direction F may be implemented in an oblique direction with respect to the ground.

The stirrer 26 may be disposed inside the transduction flow path 26. The stirrer 26 may be disposed in a horizontal direction, a vertical direction, or an oblique direction with respect to the ground. As the stirrer 26 is disposed inside the transduction flow path 25, the solution 81 may be uniformly mixed.

In FIG. 14, the transduction container 70 for accommodating the solution 81 is not used and the transduction flow path 25 is used. Thus, a large amount of the solution 81 may be irradiated with the extracorporeal shock waves W.

Referring to FIG. 14, the transduction flow path 25 may be configured to have a longitudinal direction. The extracorporeal shock wave transducer 201 connected to the transmission member 31 may be disposed at a lower portion of the transduction flow path 25. The extracorporeal shock wave transducer 201 may be provided as a plurality of extracorporeal shock wave transducers 201. The extracorporeal shock wave transducer 201 may be surrounded by the reflective plate 2010. The reflective plate 2010 may be formed in a curved shape. As the extracorporeal shock wave transducer 201 is surrounded by the reflective plate 2010, the extracorporeal shock waves W generated by the extracorporeal shock wave transducer 201 may be reflected by the reflective plate 2010 and concentrated at a predetermined position.

According to one embodiment, the extracorporeal shock wave transducer 201 connected to the transmission member 31 may be disposed on a side surface of the transduction flow path 25. The extracorporeal shock wave transducer 201 may be provided as a plurality of extracorporeal shock wave transducers 201. The extracorporeal shock wave transducer 201 may be surrounded by the reflective plate 2010. The reflective plate 2010 may be formed in a curved shape. As the extracorporeal shock wave transducer 201 is surrounded by the reflective plate 2010, the extracorporeal shock waves W generated by the extracorporeal shock wave transducer 201 may be reflected by the reflective plate 2010 and concentrated at a predetermined position.

The extracorporeal shock waves W generated by the extracorporeal shock wave transducer 201 may proceed to the medium 82. Alternatively, the extracorporeal shock waves W may be reflected by the reflective plate 2010 and proceed to the medium 82. The medium 82 may be in contact with the extracorporeal shock wave transducer 201 and accommodated in the space formed inside the reflective plate 2010. The extracorporeal shock waves W may pass through the medium 82 and the transduction flow path 25 and may be concentrated at at least a portion of the solution 81 disposed inside the transduction flow path 25. FIG. 14 illustrates the extracorporeal shock waves W that are concentrated at a center of the transduction flow path 25, but a position at which the extracorporeal shock waves W are concentrated may change according to a position of the extracorporeal shock wave transducer 201. In this way, even when the extracorporeal shock wave transducer 201 is disposed under the transduction flow path 25, the extracorporeal shock waves W may be transmitted to the solution 81 through the medium 82. Accordingly, the target substance inside the solution 81 may be loaded into the delivery vehicle. Further, a large amount of the solution 81 may be irradiated with the extracorporeal shock waves W in a short period of time.

According to the embodiment, the extracorporeal shock wave transducer 201 may be a piezo type or an electromagnetic type.

FIG. 15 illustrates a pressure change due to ultrasonic waves over time, and FIG. 16 illustrates a pressure change due to extracorporeal shock waves over time.

Extracorporeal shock waves are also a type of sound wave, but there are the following differences between extracorporeal shock waves and ultrasonic waves. Ultrasonic waves are implemented as periodic and continuous waves, but extracorporeal shock waves are implemented as non-continuous waves. Referring to FIG. 15, a pressure generated by the ultrasonic waves is constantly generated as a positive pressure and a negative pressure, the positive pressure and the negative pressure are alternately generated, and thus cavitation may not occur in a portion of the solution under pressure.

On the other hand, referring to FIG. 16, it can be identified that a pressure generated by the extracorporeal shock waves is different from the pressure generated by the ultrasonic waves. The pressure generated by the extracorporeal shock waves is generated as a positive pressure and a negative pressure, but the magnitudes of the positive pressure and the negative pressure are not the same and the positive pressure and the negative pressure are not continuously generated, and thus cavitation may occur in a portion of the solution under pressure. As cavitation occurs, a shock due to the cavitation may be transmitted to the delivery vehicle, and thus a portion of the delivery vehicle may be lost or a hole may be formed. Further, the target substance may be loaded into the delivery vehicle through the loss of the portion of the delivery vehicle or the formed hole. As a result, the target substance may be loaded into the delivery vehicle through the cavitation generated by the extracorporeal shock waves.

Although the present invention has been described with reference to the embodiments illustrated in the drawings, the description is merely exemplarily, and those skilled in the art to which the present invention belongs should understand that various modifications and other equivalent embodiments may be made. Further, the prevent invention may be used in other fields. Thus, the true technical scope of the present invention should be determined by the appended claims.

The invention claimed is:

1. An extracorporeal shock wave device for loading a target substance into a delivery vehicle, the device comprising:

an extracorporeal shock wave generator;

a transmission member connected to the extracorporeal shock wave generator;

an extracorporeal shock wave transduction unit including an extracorporeal shock wave transducer configured to convert power supplied from the extracorporeal shock wave generator through the transmission member into extracorporeal shock waves;

an inlet formed in at least a portion of the extracorporeal shock wave generator;

a transduction container in which at least one transduction container hole is formed, a refrigerant supply flow path connected to the extracorporeal shock wave transduction unit and configured to supply a refrigerant to the extracorporeal shock wave transduction unit;

a refrigerant discharge flow path connected to the extracorporeal shock wave transduction unit and configured to move the refrigerant discharged from the extracorporeal shock wave transduction unit; and a cooler connected to the refrigerant supply flow path and the refrigerant discharge flow path and configured to cool the refrigerant, wherein the extracorporeal shock wave transducer radiates extracorporeal shock waves and loads a target substance inside a solution into a delivery vehicle, wherein the solution is accommodated in the transduction container hole and the transduction container is inserted into the inlet.

2. The extracorporeal shock wave device of claim 1, wherein the extracorporeal shock wave transducer and the transduction container move relative to each other.

3. The extracorporeal shock wave device of claim 1, further comprising a protective member configured to surround at least a portion of the extracorporeal shock wave transducer, wherein the protective member and the solution are in contact with each other.

4. The extracorporeal shock wave device of claim 1, wherein the extracorporeal shock wave transducer is disposed under the transduction container, the refrigerant is disposed between the extracorporeal shock wave transducer and the transduction container, and extracorporeal shock waves generated by the extracorporeal shock wave transducer proceed to the transduction container hole.

5. The extracorporeal shock wave device of claim 1, further comprising a reflective plate configured to surround at least a portion of the extracorporeal shock wave transducer, wherein the extracorporeal shock waves generated by the extracorporeal shock wave transducer are reflected by the reflective plate and proceed to the transduction container hole.

6. The extracorporeal shock wave device of claim 1, wherein the extracorporeal shock wave transducer has a longitudinal direction, and a reflective plate has a longitudinal direction parallel to the longitudinal direction of the extracorporeal shock wave transducer.

7. The extracorporeal shock wave device of claim 1, further comprising a second extracorporeal shock wave transducer configured to convert the power supplied through the transmission member into extracorporeal shock waves and connected to the extracorporeal shock wave transducer in parallel.

8. An extracorporeal shock wave device for loading a target substance into a delivery vehicle, the device comprising:

an extracorporeal shock wave generator;

a transmission member connected to the extracorporeal shock wave generator;

an extracorporeal shock wave transduction unit including an extracorporeal shock wave transducer configured to convert power supplied from the extracorporeal shock wave generator through the transmission member into extracorporeal shock waves;

at least one supply container in which the delivery vehicle or the target substance is accommodated;

a first flow path which is connected to the supply container and the extracorporeal shock wave transduction unit and through which the delivery vehicle or the target substance accommodated in the supply container moves to the extracorporeal shock wave transduction unit;

a refrigerant supply flow path which is connected to the extracorporeal shock wave transduction unit and through which a refrigerant is supplied to the extracorporeal shock wave transduction unit;

a refrigerant discharge flow path which is connected to the extracorporeal shock wave transduction unit and through which the refrigerant discharged from the extracorporeal shock wave transduction unit moves;

a cooler connected to the refrigerant supply flow path and the refrigerant discharge flow path and configured to cool the refrigerant;

a second flow path through which the solution discharged from the extracorporeal shock wave transduction unit moves;

a pump connected to the second flow path and configured to move the solution;

a third flow path which is connected to the second flow path and through which a portion of the solution moves to a sample storage container; and a fourth flow path which is connected to the pump and a storage container and through which the solution moves to the storage container, wherein the extracorporeal shock wave transducer radiates extracorporeal shock waves and loads a target substance inside a solution into a delivery vehicle.

9. The extracorporeal shock wave device of claim 8, wherein the extracorporeal shock wave transduction unit further includes a transduction flow path through which the solution moves and which has a longitudinal direction, at least a portion of the transduction flow path is in contact with the refrigerant, and the extracorporeal shock wave transducer is in contact with the refrigerant.

10. The extracorporeal shock wave device of claim 8, wherein a longitudinal direction of a transduction flow path is parallel to a vertical direction, and the solution moves from one side to the other side of the transduction flow path.

11. The extracorporeal shock wave device of claim 8, wherein a longitudinal direction of a transduction flow path is perpendicular to a vertical direction, and the solution moves from one side to the other side of the transduction flow path.

12. The extracorporeal shock wave device of claim 8, further comprising a stirrer disposed inside a transduction flow path.

* * * * *